US00PP16021P2

(12) United States Plant Patent
van Rijn

(10) Patent No.: US PP16,021 P2
(45) Date of Patent: Oct. 4, 2005

(54) ***ANTHURIUM* PLANT NAMED 'RIJN199828'**

(50) Latin Name: *Anthurium andreanum*
Varietal Denomination: Rijn199828

(75) Inventor: Leonardus W. B. M. van Rijn, De Lier (NL)

(73) Assignee: RijnPlant B.V., De Lier (NL)

( * ) Notice: Subject to any disclaimer, the term of this patent is extended or adjusted under 35 U.S.C. 154(b) by 18 days.

(21) Appl. No.: 10/959,784

(22) Filed: Oct. 6, 2004

(51) Int. Cl.[7] ..... A01H 5/00

(52) U.S. Cl. ..... Plt./365

(58) Field of Search ..... Plt./365

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Anthurium* plant named 'Rijn199828', characterized by its large, upright and outwardly spreading plant habit; freely clumping growth habit; large, durable and dark green-colored leaves; red-colored spathes with red-colored spadices that are positioned above and beyond the foliage on strong and erect scapes; freely flowering habit; and good inflorescence longevity.

1 Drawing Sheet

Botanical classification/cultivar designation: *Anthurium andreanum* cultivar Rijn199828.

BACKGROUND OF THE INVENTION

The present invention relates to a new and distinct cultivar of *Anthurium* plant, botanically known as *Anthurium andreanum*, and hereinafter referred to by the name 'Rijn199828'.

The new *Anthurium* is a naturally-occurring whole plant mutation of *Anthurium andreanum* cultivar Leny, disclosed in U.S. Plant Pat. No. 10,272. The new *Anthurium* was discovered and selected by the Inventor as a plant within a population of plants of the cultivar Leny in a controlled environment in De Lier, The Netherlands in August, 1999.

Asexual propagation of the new cultivar by meristem culture in a laboratory in Belgium since August, 1999, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique charcteristics of the cultivar Rijn199828. These characteristics in combination distinguish 'Rijn199828' as a new and distinct cultivar:

1. Large, upright and outwardly spreading plant habit.
2. Freely clumping growth habit.
3. Large, durable and dark green-colored leaves.
4. Large, red-colored spathes with red-colored spadices that are positioned above and beyond the foliage on strong and erect scapes.
5. Freely flowering habit.
6. Good inflorescence longevity.

Plants of the new *Anthurium* are most similar to plants of the parent, the cultivar Leny. In side-by-side comparisons conducted in De Lier, The Netherlands, plants of the new *Anthurium* differed from plants of the cultivar Leny in the following characteristics:

1. Plants of the new *Anthurium* had red-colored spadices whereas plants of the cultivar Leny had white to yellow-colored spadices.
2. Plants of the new *Anthurium* had coarser spadices than plants of the cultivar Leny.

BRIEF DESCRIPTION OF THE PHOTOGRAPH

The accompanying colored photograph illustrates the overall appearance of the new *Anthurium*, showing the colors as true as it is reasonably possible to obtain in colored reproductions of this type. Colors in the photograph may differ slightly from the color values cited in the detailed botanical description which accurately describe the colors of the new *Anthurium*.

The photograph comprises a side perspective view of a typical flowering plant of the cultivar Rijn199828.

DETAILED BOTANICAL DESCRIPTION

In the following description, color references are made to The Royal Horticultural Society Colour Chart, 2001 Edition, except where general terms of ordinary dictionary significance are used. The aforementioned photograph and the following observations and measurements describe two-year old plants grown in 20-cm containers in De Lier, the Netherlands, during the summer in a glass-covered greenhouse with average day temperatures of 23° C., average night temperatures of 21° C. and light levels about 6 kilolux.

Botanical classification: *Anthurium andreanum* cultivar Rijn199828.

Parentage: Naturally-occurring whole plant mutation of *Anthurium andreanum* cultivar Leny, disclosed in U.S. Plant Pat. No. 10,272.

Propagation:

*Method*.—By meristem culture.

*Time to initiate roots on a meristem-cultured plant.*—About four weeks at 20 to 24° C.

*Time to develop roots on a meristem-cultured plant* .—About nine months at 20 to 24° C.

*Root description.*—Primary roots, thick, fleshy, dark pink to cream-colored; lateral roots, thick and abundant.

Plant description:

*Plant shape.*—Large, upright and outwardly spreading plant habit, broad inverted triangle, symmetrical.

*Growth habit.*—Freely clumping, bushy and dense growth habit; about five clumps per plant; moderately vigorous.

*Plant height, from soil level to top of leaf plane.*—About 63 cm.

*Plant height, from soil level to top of inflorescences.*—About 91 cm.

*Plant diameter or spread.*—About 81 cm.

*Foliage description.*—Arrangement: Alternate; simple. Length: About 35.1 cm. Width: About 17.6 cm. Shape: Ovate. Apex: Apiculate. Base: Cordate. Margin: Entire. Texture, upper and lower surfaces: Leathery; glabrous, smooth; durable. Venation pattern: Pinnate. Color: Developing leaves, upper surface: Closest to 200B to 200C with yellowish green overtones. Developing leaves, lower surface: Closest to 166A. Fully developed leaves, upper surface: Darker than 147A. Fully developed leaves, lower surface: 146A. Venation, upper surface: 144A. Venation, lower surface: 144C. Petiole: Length: About 42 cm. Diameter, just below geniculum: About 5 mm. Diameter, at plant base: About 7 mm. Texture, upper and lower surfaces: Smooth, glabrous; slightly glossy. Color, upper surface: 143A. Color, lower surface: 144A. Geniculum length: About 3.5 cm. Geniculum diameter: About 6 mm. Geniculum texture: Smooth, glabrous; slightly glossy. Geniculum color, upper surface: 165A. Geniculum color, lower surface: 144A. Wing length: About 5.9 cm. Wing diameter: About 5 mm. Wing color: 144A.

Inflorescence description:

*Inflorescence arrangement.*—Spathes with spadices held above and beyond the foliage. Flowering structures arise from leaf axils. Freely and continuous flowering during the autumn in De Lier, The Netherlands. Typically about five inflorescences per plant. Inflorescences not fragrant.

*Inflorescence longevity.*—Inflorescences last about two months under winter conditions and about three months under summer conditions; inflorescences persistent.

*Spathe.*—Length: About 12.2 cm. Width: About 10.5 cm. Shape: Cordate. Apex: Abruptly acute. Base: Cordate. Margin: Entire. Texture, upper and lower surfaces: Leathery; glabrous, smooth. Aspect: Cupped; roughly perpendicular from the scape. Color: When developing, front surface: 45B to 46B. When developing, rear surface: 45B; towards the base, 47B. Fully developed, front surface: 46C; color becoming closer to 50A to 50B with development. Fully opened, rear surface: 50A; towards the base, 51A.

*Spadix.*—Length: About 9.9 cm. Diameter, at apex: About 7 mm. Diameter, at base: About 1.9 cm. Shape: Columnar to conical, strongly tapering towards the apex; apex, obtuse; base, obtuse. Cross section: Rounded. Aspect: About 30° from vertical. Color: Immature: 53B to 53C. Mature: 147C with 46B.

*Flowers.*—Quantity per spadix: Numerous, about 350. Shape: Rounded. Height: Less than 0.5 mm. Diameter: About 3 mm.

*Reproductive organs.*—Androecium: Anther color: No anthers visible. Gynoecium: Stigma shape: Ovoid. Stigma color: 46B. Ovary color: 46B.

*Scape.*—Length: About 66.6 cm. Diameter: About 7 mm. Strength: Strong. Aspect: Erect to slightly outwardly slanted to about 10° from vertical. Color: Towards the base, 144A; towards the apex, 165A.

*Seed and fruit.*—Seed and fruit development has not been observed on plants of the new *Anthurium.*

Disease/pest resistance: Under commercial production conditions, plants of the new *Anthurium* have not been observed to be resistant to pathogens or pests common to *Anthurium.*

Temperature tolerance: Plants of the new *Anthurium* have been observed to tolerate temperatures from about 14 to about to 35 to 36° C.

It is claimed:

1. A new and distinct cultivar of *Anthurium* plant named 'Rijn199828', as illustrated and described.

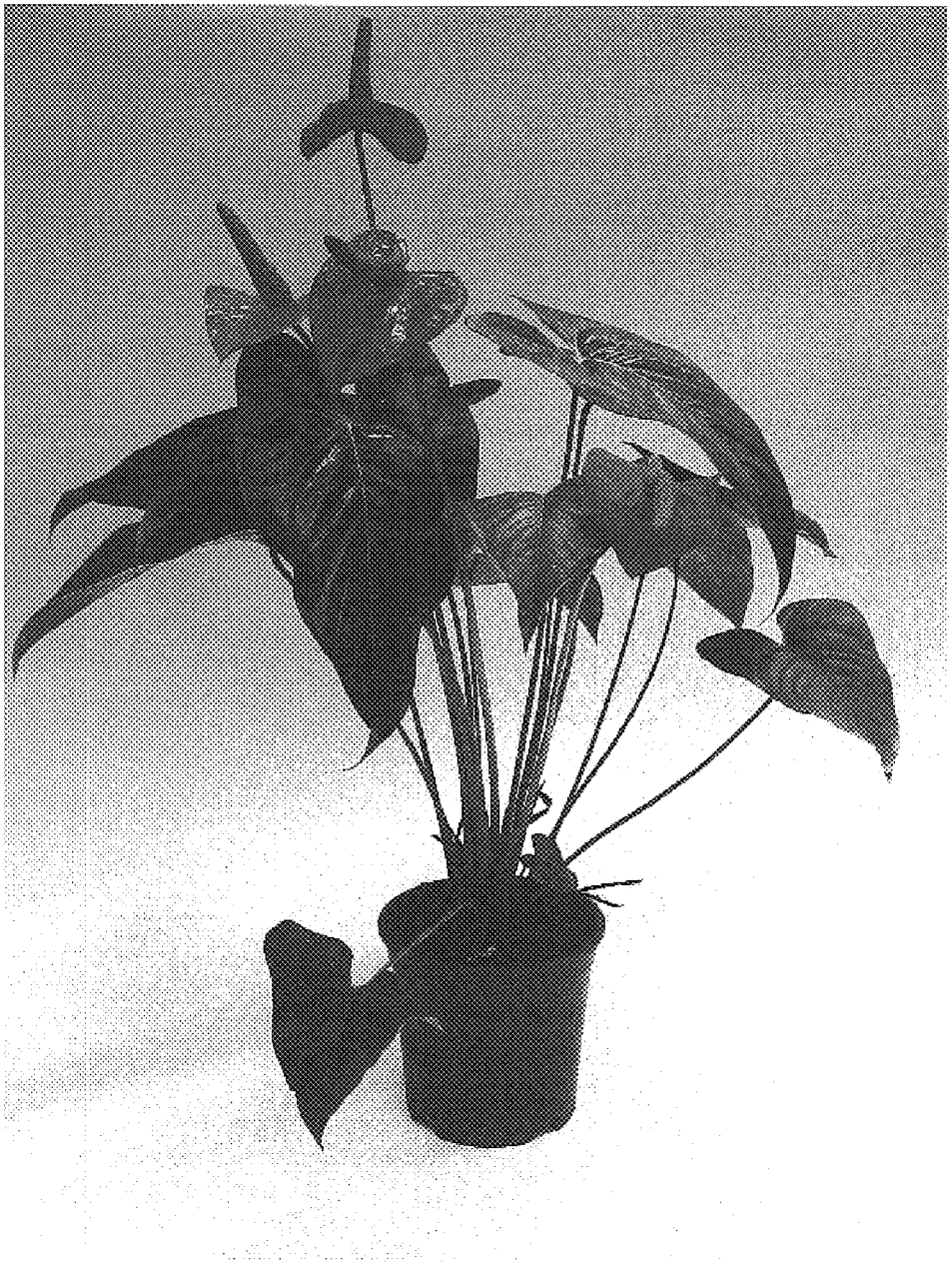

* * * * *